United States Patent [19]

Wood

[11] 4,409,150
[45] Oct. 11, 1983

[54] PREPARATION OF CYANOBENZYL CYCLOPROPANE CARBOXYLATES

[75] Inventor: Derek A. Wood, Sittingbourne, England

[73] Assignee: Shell Internationale Research Maatschappij B.V., Netherlands

[21] Appl. No.: 375,998

[22] Filed: May 7, 1982

[30] Foreign Application Priority Data

May 26, 1981 [GB] United Kingdom ................. 8116033

[51] Int. Cl.³ .......................................... C07C 121/75
[52] U.S. Cl. ................................................. 260/465 D
[58] Field of Search ................................... 260/465 D

[56] References Cited

FOREIGN PATENT DOCUMENTS 1356087 6/1974 United Kingdom .
1540632 2/1979 United Kingdom .
1559799 1/1980 United Kingdom .
2075011 11/1981 United Kingdom .

OTHER PUBLICATIONS

Itaya et al., "Synthetic Pyrethroids", ACA Symposium Series 42, pp. 45–54.
Elliott et al., Nature, vol. 28, pp. 710–711 (1974).

*Primary Examiner*—Dolph H. Torrence
*Attorney, Agent, or Firm*—Pravel, Gambrell, Hewitt, Kirk & Kimball

[57] ABSTRACT

A method for preparing a pyrethroid insecticide of general formula:

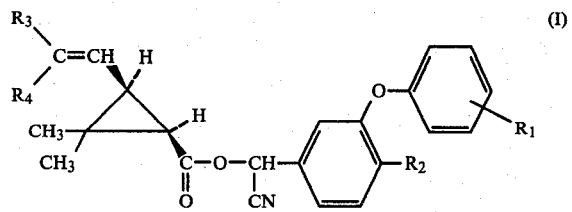

wherein the two hydrogen atoms on the cyclopropane ring are in the cis- configuration, in which an acid of formula:

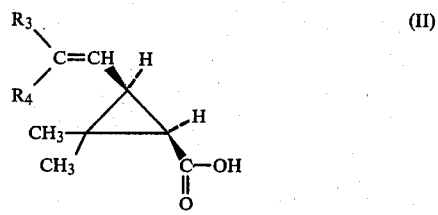

is neutralized with a water-soluble base and then reacted in the presence of a phase-transfer catalyst with a solution in a substantially water-immiscible organic solvent of an alpha-cyanobenzyl aryl sulphonate of formula:

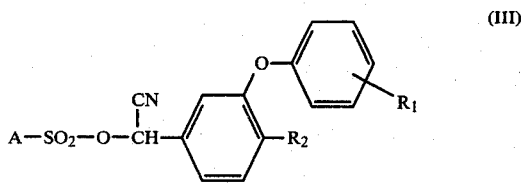

the substituents in the formulae having the following meanings; A represents an optionally substituted aryl group; $R_1$ and $R_2$ represent hydrogen or halogen; and $R_3$ and $R_4$ represent chlorine, bromine, or methyl.

6 Claims, No Drawings

PREPARATION OF CYANOBENZYL CYCLOPROPANE CARBOXYLATES

This invention relates to the preparation of synthetic pyrethroid insecticide esters by reacting a cyanobenzyl arylsulphonate with a cyclopropane carboxylic acid.

U.K. Patent Specification No. 1,540,632 discloses a process for preparing synthetic pyrethroid insecticide esters containing a 3-substituted alpha-cyanobenzyl group as the alcohol moiety wherein a 3-substituted benzaldehyde (e.g. 3-phenoxybenzaldehyde) is reacted with the appropriate acyl chloride or bromide (e.g. 3-(2,2-dichlorovinyl)-2,2-dimethylcyclopropanecarbonyl chloride) in the presence of water, a water soluble cyanide, a substantially water-immiscible aprotic solvent and a phase-transfer catalyst.

U.K. Patent Specification No. 1,559,799 discloses a process for preparing similar synthetic pyrethroid insecticide esters wherein the appropriate acid (e.g. 3-(2,2-dichlorovinyl)-2,2-dimethylcyclopropanecarboxylic acid) is neutralised with a water-soluble base and then reacted with a solution in a substantially water-immiscible organic solvent of an alpha-cyano-3-phenoxybenzyl halide in the presence of a phase-transfer catalyst.

Synthetic pyrethroid insecticide esters which are alpha-cyano-3-phenoxybenzyl 3-(2,2-di-substituted vinyl)-2,2-dimethylcyclopropanecarboxylates have eight possible isomers, since the cyclopropane ring of the acid moiety contains two centres of asymmetry and a third centre of asymmetry exists in the alcohol moiety. In general, superior pesticidal activity resides among the compounds having cis-configuration about the cyclopropane ring, as disclosed by Itaya et al. in "Synthetic Pyrethroids," ACS Symposium Series 42, Pages 45 to 54, and the isomer which has the greatest pesticidal activity is generally that isomer which is conveniently designated the 1R cis S-isomer, 1R cis-designating configuration in the acid moiety and S-designating configuration in the alcohol moiety, as described by Elliott et al. in Nature, Vol. 248, Pages 710 and 711 (1974).

Although the processes of the above two U.K. patents both give excellent results, that of U.K. Patent Specification No. 1,540,632 is economically more attractive since it employs as starting material the commercially available 3-phenoxybenzaldehyde. When cis-alpha-cyano-3-phenoxybenzyl 3-(2,2-dichlorovinyl)-2,2-dimethylcyclopropanecarboxylate is prepared from pure cis-3-(2,2-dichlorovinyl)-2,2-dimethylcyclopropanecarboxylic acid by the process of U.K. Patent Specification No. 1,540,632, it has been found that the product is typically 95% by weight pure ester which contains the cis/trans-isomers in 95:5 ratio by weight. If this product is used directly in the process described in U.K. Patent Specification No. 2,075,011, the maximum yield has been found to be 65% by weight of 95% pure 1:1 mixture of 1R cis, S- and 1S cis R-isomers of the ester.

The present invention provides a synthetic route to such pyrethroid insecticides which facilitates the production in good yields of the more active cis isomer(s) of the general formula:

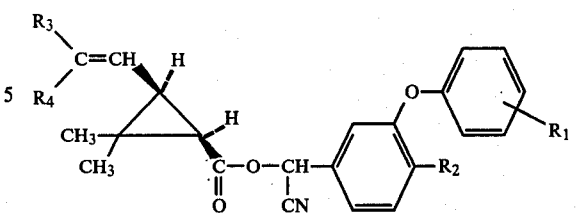

wherein the two hydrogen atoms on the cyclopropane ring are in the cis-configuration, characterised in that an acid of formula

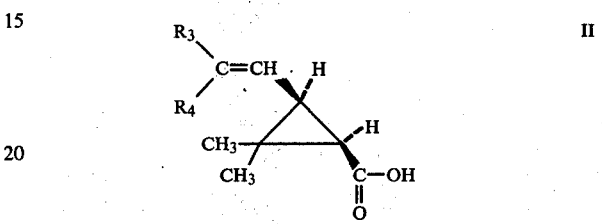

is neutralised with a water-soluble base and then reacted in the presence of a phase-transfer catalyst with a solution in a substantially water-immiscible organic solvent of an alpha-cyanobenzyl aryl sulphonate of formula:

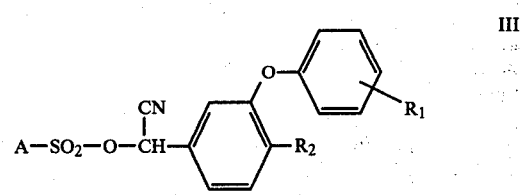

the substituents in the formulae having the following meanings; A represents an optionally substituted aryl group; each of $R_1$ and $R_2$ independently represents a hydrogen or halogen atom; and each of $R_3$ and $R_4$ independently represents a chlorine or bromine atom or a methyl group.

A may be, for example, a phenyl group substituted by one or more substituents independently selected from halogen atoms, nitro groups, and alkyl and alkoxy groups preferably containing 1 to 6 carbon atoms and optionally halogenated, suitably by fluorine, chlorine or bromine, and is conveniently a phenyl group substituted by one or more methyl groups. Advantageously A is a tolyl group.

Advantageously $R_1$ is hydrogen or bromine and $R_2$ is hydrogen or fluorine, at least one of $R_1$ and $R_2$ being hydrogen. Preferably $R_2$ and $R_2$ are both hydrogen. Preferably $R_3$ and $R_4$ are both chlorine.

Using a neutralised acid of formula II in reaction with an alpha-cyanobenzyl arylsulphonate of formula III it has been found possible to retain the cis-configuration substantially completely in preparing the pyrethroid insecticide of formula I.

The acid of formula II may conveniently be neutralised using a water-soluble inorganic base such as sodium or potassium bicarbonate, carbonate or hydroxide. Advantageously the inorganic base is sodium bicarbonate or potassium bicarbonate.

Alpha-cyanobenzyl arylsulphonates of formula III may be prepared by a process which comprises reacting a benzaldehyde of formula:

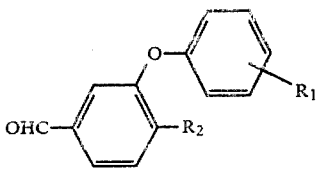

wherein $R_1$ and $R_2$ are as defined above, with an alkali metal cyanide and an arylsulphonyl halide of formula A—$SO_2$—Hal, wherein A is as defined above and Hal is fluorine, bromine or preferably, chlorine.

This process is conveniently carried out in the presence of water, a substantially water-immiscible organic solvent and a phase transfer catalyst. Potassium and, especially, sodium cyanides are the preferred alkali metal cyanides.

The phase-transfer catalyst may be any reagent which will accelerate interphase reactions in aqueous-/organic two-phase systems, the most convenient such catalysts including quaternary ammonium and phosphonium compounds. Generally economic considerations make it preferable to use quaternary ammonium compounds. Examples of suitable quaternary ammonium compounds include tetra alkylammonium halides, for example, tetra-n-butylammonium bromide, tetra-n-butylammonium chloride, cetyltrimethylammonium bromide and methyltri($C_{8-10}$alkyl)ammonium chlorides, and also methyltri-2-methylphenylammonium chloride. Alternatively, the macrocyclic polyethers known as "crown ethers" may be utilized as phase transfer catalyst. These compounds, together with their preparation, are described in the literature, for example in Tetrahedron Letters No. 18 (1972) pp. 1793–1796, and are commonly designated by reference to the total number of atoms forming the macrocyclic ring together with the number of oxygen atoms in that ring. Thus the macrocyclic polyether whose formal chemical name is 1,4,7,10,13,16-hexaoxacyclooctadecane is designated as "18-crown-6." Other types of compound which may be used as the phase-transfer catalyst include quaternary ammonium anion exchange resins (suitably in the hydroxyl form).

The concentration of catalyst used may vary widely, but at low concentrations (e.g. 1 mole % or less) a higher reaction temperature is required to complete the esterification reaction within an acceptable period of time whilst the use of higher concentrations (e.g. above 10 mole %) naturally increases the cost of the catalyst required to produce a given quantity of ester. For example, the use of 5 mole % of catalyst at 65°–70° C. will lead to a 20–30 fold reduction in reaction time as compared with the same reagent concentrations at room temperature, and reduction of the catalyst concentration to 1 mole % increases the reaction time 2–3 fold. Thus, the choice of reaction temperature and catalyst concentration are mutually interdependent, and in any individual instance will depend on the local economic factors. Those skilled in the art will appreciate that the nature of the reaction vessel and the stirring rate are other factors to be taken into account in determining optimum reaction conditions.

Preferred substantially water-immiscible organic solvents in either the preparation of the compounds of formula I or the cyanobenzyl arylsulphonate precursors of formula III include benzene, toluene, petroleum ethers, xylenes, trimethylbenzene, carbon tetrachloride and kerosene.

The invention is illustrated in the following examples.

EXAMPLE 1

(A) Preparation of alpha-cyano-3-phenoxybenzyl p-toluene sulphonate

A solution of 3-phenoxybenzaldehyde (198 g, 1.0 M) and p-toluenesulphonyl chloride (190.5 g, 1.0 M) in toluene (200 ml) was stirred under nitrogen and cooled to 0° C. A solution of sodium cyanide (51 g, 1.04 M) and tetra-n-butylammonium bromide (1.5 g, 0.005 M) in water (200 ml) was added dropwise over 45 minutes. After stirring for a further hour at 0° to 5° C., the organic phase was separated off and washed with water (2×100 ml). The toluene was evaporated off leaving an orange oil (395 g) which on crystallisation from ethanol (600 ml) at 15° C. yielded alpha-cyano-3-phenoxybenzyl p-toluenesulphonate as a pale cream crystalline solid (341 g, 89.9%) m.p. 56°–57.5° C.

(B) Preparation of cis-alpha-cyano-3-phenoxybenzyl 3-(2,2-dichlorovinyl)-2,2-dimethylcyclopropanecarboxylate from alpha-cyano-3-phenoxybenzyl p-toluene sulphonate Cis-3-(2,2-dichlorovinyl)-2,2-dimethylcyclopropane carboxylic acid (199 g, 0.95 M) was added to a solution of potassium carbonate (65.6 g, 0.475 M) in water (450 ml). Toluene (900 ml), tetra-n-butylammonium bromide (13.5 g, 0.05 M) and alpha-cyano-3-phenoxybenzyl p-toluenesulphonate (341 g, 0.9 M; prepared as described in A above) were added to the stirred mixture which was then heated at 70° C. for 3 hours. The mixture was cooled to ambient temperature and the organic phase was separated off, washed with aqueous potassium carbonate solution (2×200 ml) and water (2×200 ml), evaporated and degassed under vacuum to leave cis-alpha-cyano-3-phenoxybenzyl 3-(2,2-dichlorovinyl)-2,2-dimethylcyclopropanecarboxylate as a pale amber oil (364 g, 97.3%), containing less than 1% trans-isomers.

The purity of the cis-alpha-cyano-3-phenoxybenzyl 3-(2,2-dichlorovinyl)-2,2-dimethylcyclopropanecarboxylate was confirmed by subjection to the process described in U.K. Patent Specification No. 2,075,011. Thus the amber oil (364 g) was dissolved in triethylamine (550 ml) and stirred at 15° C. The precipitate which crystallised out was filtered off, washed with cold triethylamine (50 ml) and cold hexane (100 ml) and dried to give 268 g of white crystalline solid, m.p. 83°–84.5° C., containing 95% by weight of a 1:1 mixture of the 1R cis S- and 1S cis R-isomers of alpha-cyano-3-phenoxybenzyl 3-(2,2-dichlorovinyl)-2,2-dimethtylcyclopropanecarboxylate.

The solvent was evaporated from the filtrate and the residue (95 g) was dissolved in triethylamine (150 ml) and treated as above to give a further 41.4 g of white crystalline solid, m.p. 82°–84° C., containing 95% by weight of a 1:1 mixture of the 1R cis S- and 1S cis R-isomers of alpha-cyano-3-phenoxybenzyl 3-(2,2-dichlorovinyl)-2,2-dimethylcyclopropanecarboxylate.

Thus, in two treatment steps a 95% pure 1:1 mixture of 1R cis S- and 1S cis R-isomers of alpna-cyano-3-phenoxybenzyl 3-(2,2-dichlorovinyl)-2,2-dimethylcyclopropanecarboxylate was obtained in 85% yield based on the weight of the amber oil.

EXAMPLE 2

Cis-3-(2,2-dichlorovinyl)-2,2-dimethylcyclopropane carboxylic acid (1680 g, 8.04 M) was added to a solution of potassium carbonate (555 g, 4.02 M) in water (3800 ml). Toluene (7600 ml), tetra-n-butylammonium bromide (115 g, 0.4 M) and alpha-cyano-3-phenoxybenzyl p-toluenesulphonate (2902 g, 7.65 M; prepared as in Example 1(A) above) were added to the stirred mixture which was then heated at 70° C. for 5 hours. The mixture was cooled to ambient temperature and the organic phase was separated off, washed twice with aqueous potassium carbonate solution and twice with water, evaporated and degassed under vacuum to leave cis-alpha-cyano-3-phenoxybenzyl 3-(2,2-dichlorovinyl)-2,2-dimethylcyclopropanecarboxylate as a yellow oil (3130 g, 99%), containing less than 1% trans-isomers.

This yellow oil (3130 g) was dissolved in triethylamine (4650 ml) and stirred at 15° C. for 24 hours. The precipitate which crystallised out was filtered off, washed with cold triethylamine (750 ml) and cold hexane (1000 ml) and dried to give 173 g of white crystalline solid, m.p. 81°-83° C., containing 94% by weight of a 1:1 mixture of the 1R cis S- and 1S cis R-isomers of alpha-cyano-3-phenoxybenzyl 3-(2,2-dichlorovinyl)-2,2-dimethylcyclopropanecarboxylate.

The solvent was evaporated from the filtrate and the residue was dissolved in triethylamine (2000 ml) and treated as above to give a further 864 g of white crystalline solid, m.p. 81.5°-83.5° C., containing 94% by weight of a 1:1 mixture of the 1R cis S- and 1S cis R-isomers of alpha-cyano-3-phenoxybenzyl 3-(2,2-dichlorovinyl)-2,2-dimethylcyclopropanecarboxylate.

Concentration of the filtrate and stirring at 15° C. for 48 hours enabled a further 96 g of white crystalline solid, m.p. 82.5°-84° C., containing 95% by weight of a 1:1 mixture of the 1R cis S- and 1S cis R-isomers of alpha-cyano-3-phenoxybenzyl 3-(2,2-dichlorovinyl)-2,2-dimethylcyclopropanecarboxylate, to be obtained.

Thus in three treatment steps a 94% pure 1:1 mixture of 1R cis S- and 1S R-isomers of alpha-cyano-3-phenoxybenzyl 3-(2,2-dichlorovinyl)-2,2-dimethylcyclopropanecarboxylate was obtained in 86.2% yield based on the weight of the yellow oil.

EXAMPLES 3 TO 6

Cis-3-(2,2-dichlorovinyl)-2,2-dimethylcyclopropane carboxylic acid (22 g, 0.105 M) was added to a solution of an inorganic base in water (50 ml). Toluene (100 ml), tetra-n-butylammonium bromide (1.6 g, 5 mole % based on the cyclopropane carboxylic acid) and alpha-cyano-3-phenoxybenzyl p-toluenesulphonate (37.9 g, 0.1 M) were added to the stirred mixture which was then heated at 40°-45° C. for 24 hours. The reaction mixture was then treated as in Example 1 to yield cis-alpha-cyano-3-phenoxybenzyl 3-(2,2-dichlorovinyl)-2,2-dimethylcyclopropanecarboxylate as a pale amber oil containing less than 1% trans-isomers.

The bases, their quantities and the yields obtained are given in Table I following.

TABLE I

| Base | quantity of base | Yield (g) |
| --- | --- | --- |
| sodium hydroxide | 4.2g, 0.105M | 39.4g |
| potassium carbonate | 7.25g, 0.525M | 41.0g |
| potassium carbonate | 14.5g, 0.105M | 38.75g |
| sodium bicarbonate | 8.82g, 0.105M | 41.3g |

EXAMPLES 7 TO 9

Following the procedure of Example 6 (i.e. sodium bicarbonate as base), but using different phase-transfer catalysts (1.6 g in each case) and stirring at 40°-45° C. until reaction was complete (as determined by thin-layer chromatography), gave cis alpha-cyano-3-phenoxybenzyl 3-(2,2-dichlorovinyl)-2,2-dimethylcyclopropane carboxylate as a pale amber oil containing less than 1% trans-isomers, as indicated in the following Table II.

TABLE II

| Phase-transfer catalyst | Reaction time (hrs) | Yield (g) |
| --- | --- | --- |
| ADOGEN 464 (Trade Mark) | 30 hrs | 41.7g |
| Cetyltrimethylammonium bromide | 50 hrs | 40.85g |
| Tetrabutylammonium bromide | 22 hrs | 41.0g |

ADOGEN 464 (ex Aldrich Chemical Company) is a mixture of methyltri($C_{8-10}$ alkyl)ammonium chlorides, $n_D^{20}$ 1.4665.

EXAMPLES 10 AND 11

Following the procedure of Example 9 but using carbon tetrachloride (100 ml) in place of toluene, and using tetrabutylammonium bromide (1.6 g) as catalyst, gave cis-alpha-cyano-3-phenoxybenzyl 3-(2,2-dichlorovinyl)-2,2-dimethylcyclopropane carboxylate as a pale amber oil containing less than 1% trans-isomers, as indicated in the following Table III.

TABLE III

| Reaction temperature (°C.) | Reaction time (hrs) | Yield (g) |
| --- | --- | --- |
| 40–45° C. | 20 hours | 41.25g |
| 63–66° C. | 3 hours | 39.9g |

COMPARATIVE EXAMPLE

Cis-alpha-cyano-3-phenoxybenzyl 3-(2,2-dichlorovinyl)-2,2-dimethylcyclopropanecarboxylate was prepared by the process of U.K. Patent Specification No. 1,540,632 as follows. A solution of sodium cyanide (980 g, 20 M) and tetrabutylammonium bromide (0.5 g, 0.01 M) in water (3835 ml) was added to a stirred mixture of 3-phenoxybenzaldehyde (3305 g, 16.69 M) and cis-3-(2,2-dichlorovinyl)-2,2-dimethylcyclopropanecarbonyl chloride in toluene (17 liters) over a period of 3 hours whilst maintaining the temperature of the mixture in the range 10° to 12° C.

The mixture was stirred for 7 hours, more tetrabutylammonium bromide (11 g, 0.22 M) was added and the mixture was stirred overnight. The aqueous layer was removed from the mixture and the organic phase was washed successively with 5% aqueous potassium carbonate solution and with demineralised water and was evaporated under reduced pressure to yield alpha-cyano-3-phenoxybenzyl 3-(2,2-dichlorovinyl)-2,2-dimethylcyclopropanecarboxylate (7.0 kg) as a pale amber oil which was shown by high-performance liquid chromatography to contain 95% cis-isomers: 5% trans-isomers (w/w).

This 95:5 mixture of cis- and trans-isomers was subjected to the process described in U.K. patent application No. 8,112,344. Thus the amber oil was dissolved in triethylamine (10.5 liters) and stirred at 15° C. for 5 days. The crystalline precipitate which formed was filtered off, washed with cold triethylamine and cold hexane and dried to give 4.5 kg of white crystalline solid, m.p. 83.5°-85.5° C., containing 95% by weight of a 1:1 mixture of the 1R cis S- and 1S cis R-isomers of alpha-cyano-3-phenoxybenzyl 3-(2,2-dichlorovinyl)-2,2-dimethylcyclopropanecarboxylate.

The solvent was evaporated from the filtrate and the residue (2.5 kg) was dissolved in triethylamine (3.75 liters), stirred for 21 days at 15° C. and treated as above to isolate the white crystalline solid, which amounted to 25 g, had m.p. 83.5°-85.5° C. and contained 95% by weight of a 1:1 mixture of the 1R cis S- and 1S cis R-isomers of alpha-cyano-3-phenoxybenzyl 3-(2,2-dichlorovinyl)-2,2-dimethylcyclopropanecarboxylate.

Thus in the two treatment steps the 95% pure 1:1 mixture of 1R cis S- and 1S cis R-isomers of alpha-cyano-3-phenoxybenzyl 3-(2,2-dichlorovinyl)-2,2-dimethylcyclopropanecarboxylate was obtained in overall yield of only 65% based on the weight of the amber oil.

Similar experiments in which the amber oil contained 6% and 10% of trans-isomers gave corresponding respective overall yields of 95% pure 1:1 mixtures of 1R cis S- and 1S cis R-isomers of alpha-cyano-3-phenoxybenzyl 3-(2,2-dichlorovinyl)-2,2-dimethylcyclopropanecarboxylate of only 63% and 36% by weight of the amber oils.

I claim:

1. A method for preparing a pyrethroid insecticide of general formula:

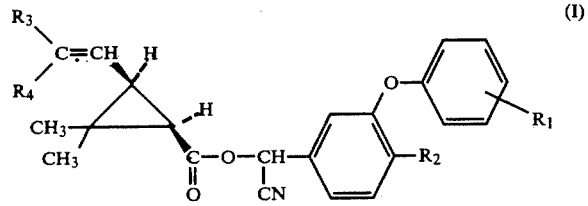

wherein the two hydrogen atoms on the cyclopropane ring are in the cis-configuration, characterised in that an acid of formula

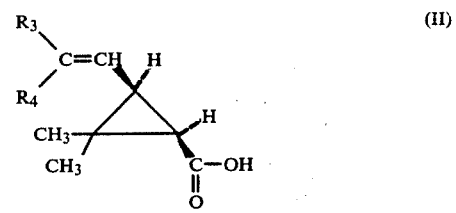

is neutralised with a water-soluble base and then reacted in the presence of a phase-transfer catalyst with a solution in a substantially water-immiscible organic solvent of an alpha-cyanobenzyl aryl sulphonate of formula:

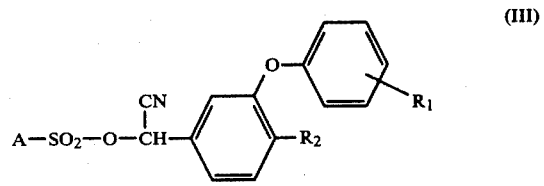

the substituents in the formulae having the following meanings; A represents an optionally substituted aryl group; each of $R_1$ and $R_2$ independently represents a hydrogen or halogen atom; and each of $R_3$ and $R_4$ independently represents a chlorine or bromine atom or a methyl group.

2. A method as claimed in claim 1 wherein $R_1$ and $R_2$ are both hydrogen atoms and $R_3$ and $R_4$ are both chlorine atoms.

3. A method as claimed in claim 1 or 2 wherein A is a tolyl group.

4. A method as claimed in any one of claim 1-3 wherein the phase transfer catalyst is a quaternary ammonium compound or a macrocyclic polyether.

5. A method as claimed in claim 4 wherein the phase transfer catalyst is a tetraalkyl ammonium halide.

6. A method as claimed in any one of the preceding claims wherein the organic solvent is toluene or carbon tetrachloride.

* * * * *